United States Patent [19]

Hetrick

[11] 4,272,331
[45] Jun. 9, 1981

[54] OSCILLATORY MODE OXYGEN SENSOR AND METHOD

[75] Inventor: Robert E. Hetrick, Dearborn Heights, Mich.

[73] Assignee: Ford Motor Company, Dearborn, Mich.

[21] Appl. No.: 126,607

[22] Filed: Mar. 3, 1980

[51] Int. Cl.³ .......................................... G01N 27/58
[52] U.S. Cl. ................................. 204/1 T; 204/195 S; 204/1
[58] Field of Search ............................ 204/195 S, 1 S; 123/438, 489; 324/71 R

[56] References Cited

U.S. PATENT DOCUMENTS

| | | | |
|---|---|---|---|
| 3,562,521 | 2/1971 | Vanderschmidt et al. | 250/43.5 |
| 3,738,341 | 6/1973 | Loos | 123/119 R |
| 3,948,081 | 4/1976 | Wessel et al. | 73/23 |
| 4,066,528 | 1/1978 | Mansfield | 204/195 T |
| 4,111,776 | 9/1978 | Mansfield | 204/195 T |
| 4,112,893 | 9/1978 | Anzai | 123/119 EC |
| 4,169,440 | 10/1979 | Taplin | 123/119 EC |

*Primary Examiner*—G. L. Kaplan

*Attorney, Agent, or Firm*—Peter Abolins; Clifford L. Sadler

[57] ABSTRACT

This specification discloses a device to determine the partial pressure of oxygen in a gaseous atmosphere. The device, which is immersed in the atmosphere, is constructed to define an enclosed volume in which the atmosphere can be established by means of a small leak. The enclosing structure contains two partitions which can conduct oxygen ions and act as electrochemical cells. One partition is called the pump cell while the other is called the sensor cell. When attached to an external power supply, the current ($I_P$) drawn through the pump cell either adds or removes (from or to the ambient) gaseous oxygen from the volume. As a result of the pumping action, an EMF ($V_S$) develops across the sensor cell which can be used to measure the change in oxygen partial pressure in the volume relative to the ambient. An external circuit causes a pump current to flow which removes oxygen from the volume until $V_S$ reaches a reference voltage. Then, pumping is reduced or reversed until $V_S$ reaches a second reference voltage. The pumping pattern is caused to repeat indefinitely establishing an oscillatory period that is proportional to oxygen partial pressure.

8 Claims, 8 Drawing Figures

OSCILLATORY MODE OXYGEN SENSOR AND METHOD

BACKGROUND OF THE INVENTION

1. Field of the Invention

This invention relates to determining the concentration of oxygen in a gaseous atmosphere.

2. Prior Art

U.S. Pat. Nos. 3,907,657 to Heijne and 3,514,377 to Spacil et al relate to the measurement of oxygen ($O_2$) concentrations using solid electrochemical devices. For applications at elevated temperatures (>500° C.), for example, as might be encountered in the exhaust gases of furnaces or automobiles, the active material in these devices may be ceramic zirconium dioxide suitably adapted for the conduction of $O^=$ ions. Electrochemical cells made from this material are suitable at elevated temperature for oxygen sensing and pumping applications.

The mode of operation of the Heijne device can be described as an oxygen counting mode in which oxygen partial pressure is determined on a sampling basis. A constant current (or equivalent means) is applied to an electrochemical cell which forms part of the enclosure of a volume for a period of time, $t_p$, for the purpose of electrochemically pumping out most of the oxygen from that volume. The ambient atmosphere has established itself within the volume prior to the pump out, by means of a leak. An additional electrochemical cell, which serves as a sensor of the reduced oxygen partial pressure within the volume and which also constitutes a portion of the enclosure, provides a signal indicating when oxygen has been sufficiently depleted from the volume (see FIG. 4 of Heijne). Knowing the temperature, enclosed volume, the pump out current and time allows one to calculate the number of oxygen molecules within the enclosure from the ideal gas law. The number of oxygen molecules is in turn proportional to the desired oxygen partial pressure. If a constant pump current is used, the pump out time ($t_p$) is proportional to the oxygen partial pressure. If a constant current is not used, then the integral of the pump out current over the pump out time is proportional to the oxygen partial pressure.

The Heijne device can provide an output which is linearly proportional to the oxygen partial pressure. This is superior, for example, to single oxygen concentration cells used as sensors which give an output (EMF) proportional to the natural logarithm of the oxygen partial pressure $\ln(P_{O_2})$.

A potential disadvantage of the Heijne device is response time. For this measurement procedure, the leak connecting the ambient to the enclosed volume must be small so that during the pump out of oxygen, no significant amount of oxygen leaks into the volume to cause an error in the count of molecules (i.e., to erroneously increase $t_p$). However, if the leak is made small, it may take a long time, $t_v$, for the ambient to reestablish itself within the volume after a pump out. If the changes in the oxygen partial pressure in the ambient occur rapidly with respect to this time, then the device would not be able to follow these changes with repetitive operation.

U.S. Pat. Nos. 3,923,624 to Beckmans et al, 3,654,112 to Beckmans et al, and 3,907,657 to Heijne et al describe tubular ceramic structures for measuring and controlling the composition of oxygen in a carrier gas. In some cases a pump cell and a sensor cell are used. U.S. Pat. Nos. 3,923,624 and 3,654,112 teach devices to be used primarily to dose a gas with oxygen to a constant partial pressure. Measurement of the dosed gas is made by a standard technique using a zirconium dioxide oxygen concentration cell to be sure that the dosed gas contains the correct amount of oxygen. The sensitivity of the concentration cell to the oxygen partial pressure is low, being proportional to $\ln(P_{O_2})$. This purpose is divergent from the purpose of measuring with high sensitivity the oxygen partial pressure in a feedgas as would be required in an automotive application. There is no suggested application of these devices for an auto exhaust application.

In the case of the teachings of U.S. Pat. No. 3,698,384 to Jones, the purpose is to measure oxygen partial pressure in a feedgas. This is done by measuring the pumping current while holding the sensor cell voltage a constant. However, to achieve a result in the disclosed open ended tubular structure made from zirconium dioxide the flow rate of the feedgas must be kept constant. If the flow rate should attempt to vary, there is a relatively elaborate flow control circuit to keep the flow rate a constant. This scheme, which also employs a reference atmosphere is relatively unsuitable for application in an auto exhaust where the exhaust flow rate would change substantially with RPM.

U.S. Pat. Nos. 3,347,735 to McKee and 3,857,771 to Sternberg both describe oxygen sensing procedures or devices wherein the taking of a first derivative of an output signal either determines the oxygen partial pressure or can yield information on the medium which contains the oxygen. Neither device would be suitable for the continuous or repeated determination of the oxygen partial pressure in a variable, high temperature environment like that occurring in an automotive exhaust.

FIGS. 1 and 2 of the drawings illustrate a known oxygen pumping sensor in which ionically conducting zirconium dioxide with thin platinum electrodes 2 and 3 form an electrochemical cell which with additional ceramic structure 4 defines an enclosed volume 6. The ambient atmosphere can establish itself within the volume by means of a leak opening 5. A battery 7 is attached to the electrodes by means of lead wires 8 and 8'. A voltmeter 10 and ammeter 9 are provided to determine the voltage drop across the pump cell and the current flowing through it. Although similar in structure to FIG. 5 of U.S. Pat. No. 3,907,657, the operation is different. Here one applies a pump voltage V to remove oxygen from an enclosed volume 6 until the pump current saturates. The saturated current is proportional to oxygen concentration. This saturation property is shown in FIGS. 3 and 4.

This is a steady-state device. When steady state is reached, the flow of oxygen through leak opening 5 equals the pump current times a proportionality constant. The current saturates at a voltage greater than about 0.5 V because the leak in combination with the platinum electrode 2, the cathode, will only allow a limited (saturated) amount of oxygen to enter and be electrochemically pumped from the volume per unit time. The device has the advantage of giving an output signal (the value of the limiting current) which is linearly proportional to the desired ambient the oxygen partial pressure. However, to the extent that the saturated current value depends on the detailed properties of the electrode 2, the device calibration may be subject to drift as these detailed properties may change during the sintering and wear of this thin layer.

An important application of high temperature oxygen sensors is in the determination of the stoichiometric air fuel mixture in the exhaust gases of hydrocarbon fired furnaces or engines such as automobile internal combustion engines. The stoichiometric mixture is one in which the mass of air present contains just enough oxygen to react with the mass of hydrocarbons present so that there is the minimum amount of both oxygen and hydrocarbons remaining. For common automotive gasoline, the air fuel ratio (A/F=mass of air/mass of fuel) at the stoichiometric point is approximately 14.6. If, for example, an engine were running lean of stoichiometry (A/F>14.6) there would be an excess of air in the "charge" and the exhaust gas would contain a substantial oxygen partial pressure. If rich operation were occurring, e.g., an air fuel ratio less than 14.6, the exhaust gas would contain unreacted or partially reacted hydrocarbons and very low oxygen partial pressure. In particular, the equilibrium oxygen partial pressure in the exhaust gas can change by a great amount (as much as 20 orders of magnitude) as one moves from lean to rich operation. This large change forms the basis for detecting the stoichiometric air fuel ratio with an exhaust gas oxygen sensor. The electrical output of such a sensor can then be fed back to an electrically controllable carburetor or fuel injection system for maintaining engine operation always at the stoichiometric point. Depending on engine type, operation at this point frequently offers a reasonable compromise for minimizing regulated exhaust gas emissions and maximizing engine performance.

There are known high temperature oxygen sensors utilizing oxygen eletrochemical concentration cells (usually made from zirconium oxide) and requiring the use of a reference atmosphere (usually air) which are suitable for determining the stoichiometric air fuel. These devices give an output (EMF) proportional to ln oxygen partial pressure. Despite their low sensitivity to oxygen partial pressure, the large change in oxygen partial pressure at the stoichiometric point allows their useful implementation.

For some engines it is useful to operate lean of the stoichiometric A/F for the purpose of reducing fuel consumption. Oxygen partial pressure varies in a systematic way in the lean region and this can form the basis for determining lean A/F. The exact knowledge of lean A/F would be useful to fully implement a lean burn engine strategy which would maximize fuel economy and engine performance and minimize regulated emissions. However, the variation in oxygen partial pressure in the appropriate lean A/F region, e.g., air fuel ratio is greater than 16 and less than 20, is not large, (in comparison to the changes occurring near stoichiometry) so that suitable oxygen sensors with sensitivities greater than ln oxygen partial pressure are desirable for accurate measurement in the desired A/F range. These are some of the problems this invention overcomes.

SUMMARY OF THE INVENTION

In accordance with an embodiment of this invention, a ceramic electrochemical structure with associated external circuitry is capable of measuring oxygen partial pressure in a high temperature surrounding environment such as may be found in an automotive exhaust. The measurement includes use of a repetitive electrical output signal whose period is proportional to the oxygen partial pressure. The structure includes two oxygen ion ($O^=$) conducting electrochemical cells, a pump cell and a sensor cell, which in part provide the enclosing structure of a nearly enclosed volume. A leak in the enclosing structure permits an ambient atmosphere with an unknown oxygen partial pressure to establish itself within the volume.

In operation, the external circuitry causes a repetitive sequence of oxygen pumping currents to flow in the pump cell in response to EMF inputs from the sensor cell. In particular, the output of the external circuitry causes a pump cell current to flow which withdraws oxygen from the volume and returns it to the ambient atmosphere until the EMF induced on the sensor cell because of the reduced oxygen partial pressure in the volume equals some predetermined reference value. At that point, logic elements require the sign of the pump cell current to change causing oxygen to be pumped into the volume until the sensor cell EMF reaches another predetermined reference value which is algebraically less than the former reference value. At this point the logic elements cause the sign of the pump cell current to reverse and the process repeats itself indefinitely in the manner of a limit cycle oscillation. If the magnitudes of the pump cell currents are held fixed, the period of the oscillation is proportional to the oxygen partial pressure. This is because it takes increasing time to modify the inner relative to the outer oxygen partial pressure as the outer oxygen partial pressure increases. This relationship is the basis of sensor operation.

If the pump cell current is large at a given oxygen partial pressure level, oxygen pump in/out is rapid and the approach of the sensor cell EMF toward the respective reference voltages is linear. In this regime the perior is linearly proportional to oxygen partial pressure. However, if the pump cell current is reduced, the approach of the sensor cell EMF to the reference levels begins to increase exponentially in time. Thus for a limited but adjustable range of oxygen partial pressure, the device can produce an output with a much higher sensitivity than is afforded by a linear dependence on oxygen partial pressure. This higher sensitivity is advantageous.

DETAILED DESCRIPTION OF THE DRAWING

This disclosure teaches a solid electrochemical device, attached circuitry and a measurement technique for measuring oxygen partial pressure in a high temperature gaseous environment such as may be found in an automotive exhaust. In the latter environment as an example, the electric output of the device, which increases monotonically with the desired oxygen partial pressure, may be used in the feedback control of the air-to-fuel ratio of the automotive engine especially under lean operating conditions.

Figure 1:
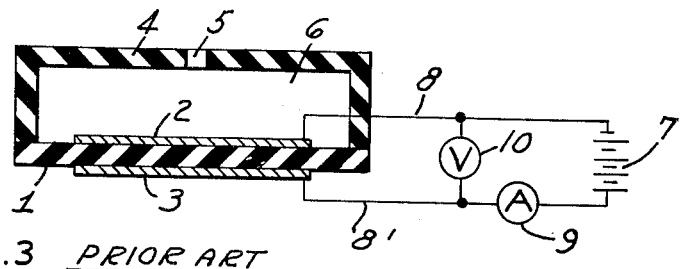
FIGS. 1 through 4 are prior art drawings with FIGS. 1 and 2 showing the construction of an electrochemical oxygen pumping device and FIGS. 3 and 4 show graphical representation of characteristics of the device.
Figure 2:
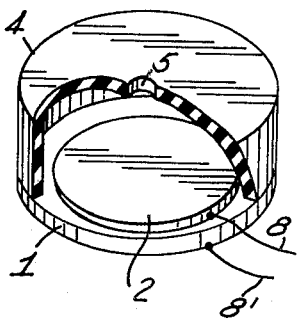
Figure 3:
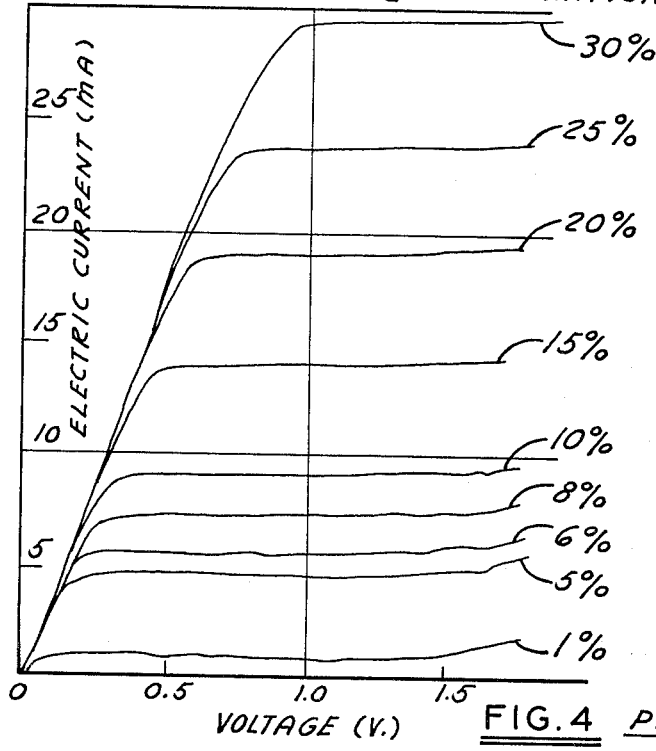
Figure 4:
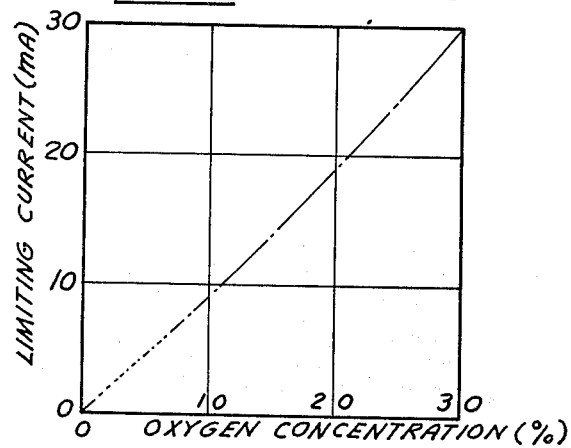
Figure 5A:
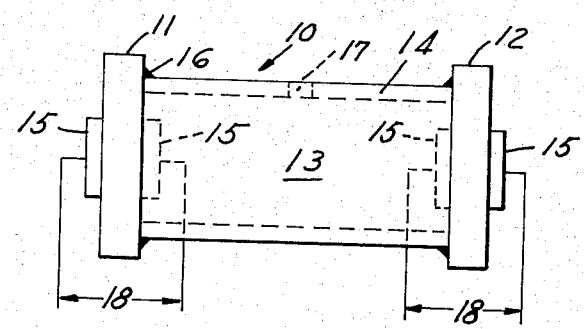
FIG. 5a is a schematic diagram of a portion of a device in accordance with an embodiment of this invention.
Figure 5B:
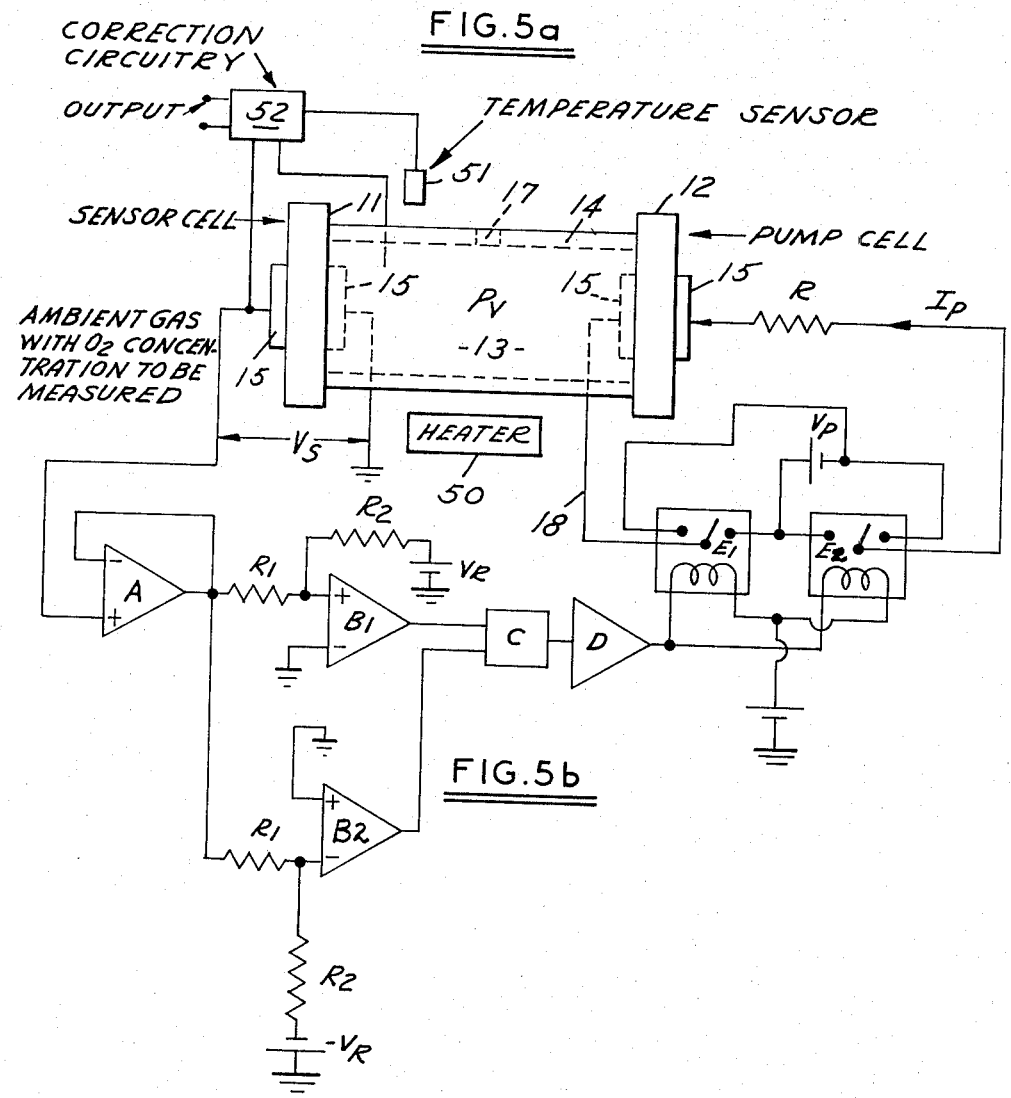
FIG. 5b is a schematic diagram similar to FIG. 5a with the addition of external circuitry for the measurement of oxygen partial pressure in an ambient gas.

As shown in the embodiment of FIGS. 5a and 5b, a device 10 consists in part of two platelets, 11 and 12 of zirconium dioxide suitably adapted for the conduction of $O^=$ ions. Such a solid ionic conductor is called a solid electrolyte. Electrodes 15 are attached to opposing faces of each platelet to form electrochemical cells. The right hand cell is termed the pump cell and the left hand cell the sensor cell to reflect their functions. The electrodes consist of platinum films (typically applied by common sputtering techniques) with a typical thickness of 1.0 micron, or other material adapted for the purpose. Lead wires 18 are affixed to each electrode so that external circuitry may be applied to the cells. Using glass frits or ceramic glue 16, the zirconium dioxide platelets are joined by a hollow, non-porous ceramic tube 14 to define an enclosed volume 13. The joining is effected so that one electrode from each cell will form a portion of the surface enclosing the volume. A small hole 17 can be drilled into the ceramic tube to allow the ambient atmosphere to establish itself within the voloume. Alternatively, the seals between the zirconium dioxide and the tube can be made somewhat leaky for the same purpose. The cells must be operated at an elevated Temperature ($\gtrsim 500°$ C.) so that the electrolyte is suitably conducting. Other embodiments may incorporate other $O^=$ conducting solid electrolytes (ex. $CeO_2$ adapted for the purpose) which can perform the desired electrochemical functions at lower temperatures. The device is completely immersed in the atmosphere whose percentage of oxygen is to be determined.

Electrochemically, if a battery $V_P$ initiates a pump current $I_P$, in the pump cell, gaseous oxygen will be withdrawn or injected into the enclosed volume 13 depending on the direction of the current flow. Before pumping, the oxygen partial pressure, $P_V$, within volume 13 will equal the ambient oxygen partial pressure $P_A$ because of the leak aperture. After pumping $P_V$ will increase or decrease relative to $P_A$ depending on the direction of $I_p$. If $I_p$ were applied indefinitely, a change in $P_V$ would occur for a transient time until it eventually reached some steady state value where the rate at which oxygen leaks into or out of volume 13 through aperture 17 equals the corresponding pumping rate. For the oscillatory mode sensor, operation is restricted to the transient pumping region.

Due to the pump induced partial pressure differences between $P_V$ and $P_A$, and EMF (labeled $V_S$) will develop across the sensor cell given by the familiar Nernst equation.

$$V_S = (RT/4F) \ln (P_A/P_V) \tag{1}$$

where R and F are the ideal gas and Faraday constants, respectively, and T is the absolute temperature. The key point is that for a given $I_P$, the rate at which $P_V$ and hence $V_S$ changes during the transient pump in/out period depends on the oxygen partial pressure initially present. For example, if the initial pressure ($P_V = P_A$) is high, it will take a longer time to pump out volume 13 to a point where $V_S$ reaches some arbitrary value, say $V^+$, than if the initial pressure is lower. This difference in time can be made the basis of an oxygen sensor.

Electrical operation for the oscillatory mode can be discussed in terms of FIG. 5b which shows the structure wired to an external circuit. The circuit is representative of one which causes $I_P$ to alternate sign periodically in response to having reached alternate reference levels, $V^+$ and $V^-$, which are also specified within the circuitry. In particular, the output of the sensor is first applied to operational amplifier A acting as a voltage follower. This unit gain "buffer" amplifier assures that the external circuit itself will not affect the sensor EMF. The output of amplifier A is fed to the dual operational amplifiers $B_1$ and $B_2$ which act as voltage comparators defining the reference levels $V^+$ and $V^-$. For example, the output of amplifier $B_1$ changes from a high to low voltage when $V_S$ reaches $V^- = -V_R(R_1/R_2)$.

Similarly, the output of amplifier $B_2$ switches from high to low as $V_S$ reaches or exceeds $V^+ = +V_R(R_1/R_2)$. The values $V^+$ and $V^-$ can be separately varied by adjusting $V_R$, $R_1$ and $R_2$ for each comparator. The outputs of $B_1$ and $B_2$ are fed to the flip-flop C which produces a high output when $V_S$ is at or below $V^-$ and a low output when $V_S$ is at or above $V^+$. This is the essential logic necessary to correctly switch $I_P$ at the reference levels. The output of flip-flop C is fed to the driver D which has sufficient output power to alternately activate the dual single pole, double-throw switches $E_1$ and $E_2$. The pump power supply $V_P$ is hooked to the switches so that simultaneous alternate throws of the switches causes the direction of $I_P$ to change through the pump. The magnitude of $I_P$ can be determined by measuring the voltage drop across the known resistor R.

Figure 6:
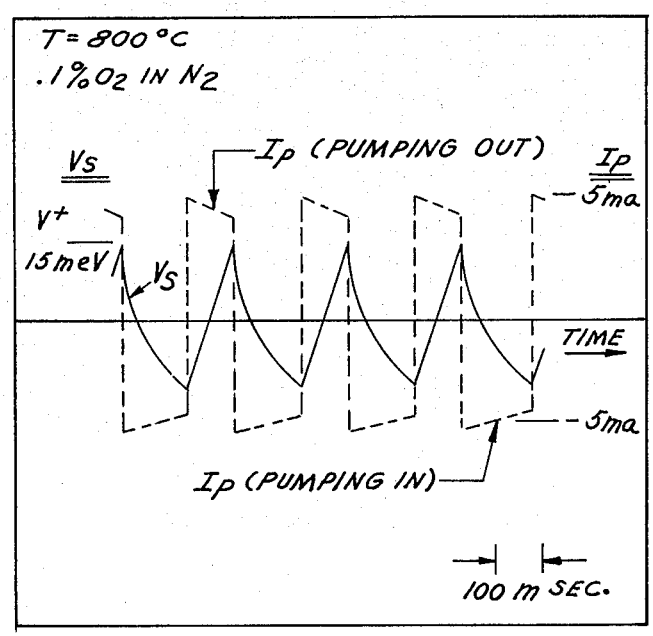
FIG. 6 shows a schematic plot of pump cell current and sensor EMF versus time during oxygen sensing operation.
Figure 7:
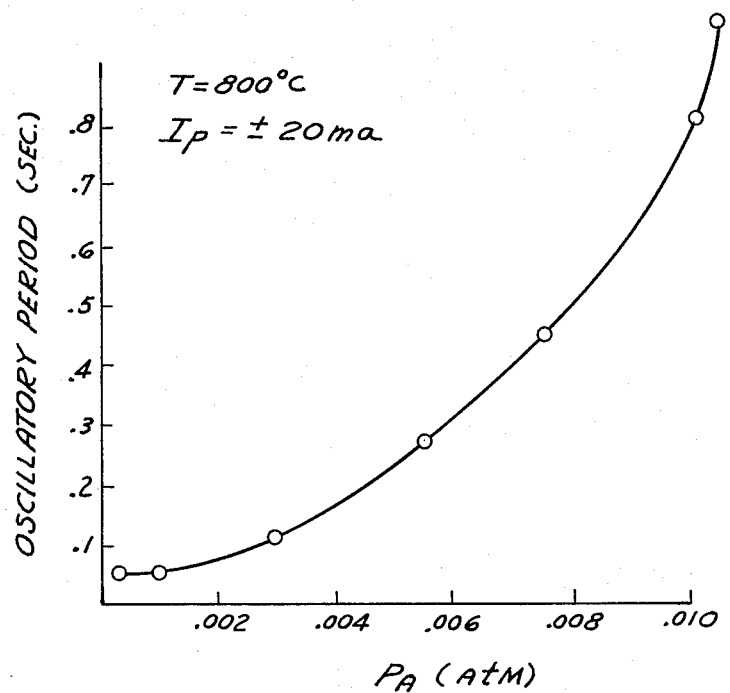
FIG. 7 shows a plot of oscillatory period versus oxygen partial pressure for a typical device.

FIG. 6 shows the type of periodic response for both $V_S$ and $I_P$ which can result if the above procedure is followed. Here the approximate value of the pump current is 5 ma while $V^\pm = \pm 15$ meV. The device is operated at T=800° C. in an atmosphere containing 0.1% oxygen in a carrier gas of $N_2$. The volume 13 was approximately $7 \times 10^{-2} cm^2$. The oscillatory period, $\tau$, was 260 msec. FIG. 7 shows that the period increases monotonically with $P_A$ and that the dependence is more than linear as $P_A$ increases.

Referring to FIG. 6, as $P_A$ increases the slope of $V_S$ with respect to time decreases leading to an increase in T. As $P_A$ increases further, $V_S$ develops curvature as a function of time and because of this takes an increasingly greater time to reach a reference level. In FIG. 6 this curvature is in evidence during the downward (pump in) portion of $V_S$ VS versus time plot. This affords high sensitivity to $P_A$ for a restricted range of $P_A$ values. If $P_A$ is increased too far, $V_S$ will come to a steady state value before a reference level is reached and oscillation will not occur. The region of high sensitivity which may be advantageous in some applications, can be adjusted by a judicious choice of $I_P$ and/or $V^+$ and $V^-$.

Factors such as T, $I_P$, $V^+$, $V^-$ and the sizes of volume 13 and the leak aperture 17 act to determine the oscillation period for a given $P_A$. The optimization of these parameters for a given application can be pursued with a simple rate equation analysis of the pumping process where the gases are assumed to obey the ideal gas law (an excellent approximation at the temperatures of interest). The rate equation is given by Equation (2).

$$(dN_V/dt) = (I_P/4e) + \sigma_L(P_A - P_V) \tag{2}$$

where $N_V$ is the number of oxygen molecules within the volume. $N_V$ is altered by two terms the first of which is the pumping term represented by $I_P$ where the factor $4e$ converts the pump current in amps to an equivalent number of oxygen molecules per second. The second term in Eq. (2) is the leakage term which occurs principally by the diffusion of oxygen in its carrier gas (e.g., $N_2$ or $CO_2$) and is proportional to the difference between $P_A$ and $P_V$. The proportionality constant is represented by $\sigma_L$ which specifies the conductance of the leak to oxygen diffusion. $\sigma_L$ increases with leak aperture and temperature and depends somewhat on the carrier gas. Assuming $P_V$ to be uniform throughout the enclosed volume, $N_V$ can be related to $P_V$ by the ideal gas law and the rate equation solved for the conditions imposed on $I_P$ and $P_V$ by the external circuitry (conditions on $P_V$ are related to those on $V_S$ by Eq. 1). Once the time dependence for $P_V$ has been found, that for $V_S$ can be obtained by Eq. 1 for comparison with experimental results. The analysis gives good agreement with experiment except in the limit of very low $P_A$ or very high $I_P$. Here the model analysis breaks down because $P_V$ is no longer constant throughout the volume. Rather $V_S$ begins to lag further behind $I_P$ because the oxygen partial pressure changes near the enclosed sensor cell electrode (which determines $V_S$) lag behind the changes occurring at the enclosed pump cell electrode. The lag is proportional to $l^2$, where $l$ is the distance between the two enclosed electrodes, and inversely proportional to the diffusion coefficient of oxygen in its carrier gas. As a consequence of the lag, the minimum period approaches a finite limiting value (rather than zero as the model would predict) as $P_A$ decreases or as $I_P$ increases.

In a practical device, a curve similar to FIG. 7 is determined using calibrated gases and serves as a calibration curve of the device for use over a range of $P_A$ values of interest. Additional circuitry of a standard character would be necessary to measure the oscillation period (by monitoring $V_S$ for example) and convert it to an electrical form (a voltage proportional to that period for example) convenient for a particular application.

The oscillation period is roughly proportional to $T^{-2}$ but the exact value depends on several parameters including the values of the reference voltages. To facilitate accuracy, it may be advantageous to account for the effects of changes in the temperature of the ambient atmosphere. This can be done in two ways. Firstly, referring to FIG. 5b, a heater 50 is used to maintain the temperature of device 10 and its adjacent gaseous surroundings within a sufficiently narrow range of values that a predetermined accuracy of the oxygen partial pressure measurement can be maintained with a single calibration constant appropriate for that narrow range of temperatures. As a given application requires, the "heater" may include a more elaborate electrical heating system in which a temperature sensor in the vicinity of the device, such as a thermocouple, provides the input to an electrical temperature regulator whose output activates the heater to a variable degree sufficient to maintain the temperature sensor output (or equivalently, the temperature) equal to some constant reference value preset in the regulator. Alternately, a temperature sensor 51 may be used to form one input of temperature correction circuitry 52 whose other input is $V_S$. The purpose of the circuitry is to correct the period of $V_S$ for the changes in the device calibration constant resulting from changes in the temperature. The output of the circuitry can be a convenient electrical quantity, such as a voltage, whose magnitude is proportional to oxygen partial pressure regardless of temperature. Depending on the application, the correction circuitry may need to encompass the facilities of a small computer.

Persual of this measurement concept shows that the reference levels need not have equal but opposite values, nor even opposite signs, nor must the pump cell current change sign (as was the case in the above example) for the oscillatory period to produce an output that can provide a useful measure of oxygen partial pressure. Rather, the reference levels may be chosen over a range of values as may be convenient.

Various modifications and variations will no doubt occur to those skilled in the various arts to which this invention pertains. For example, the electrodes may vary in shape from those described herein. These and all other variations which basically rely on the teachings through which this disclosure has advanced the art are properly considered within the scope of this invention.

I claim:

1. An electrochemical apparatus for making a measurement of oxygen partial pressure in an ambient environment including other gaseous materials, said electrochemical apparatus including:
   a solid electrochemical pump cell;
   a solid electrochemical sensor cell;
   an associated supporting structure which in combination with said pump and sensor cells defines an enclosed volume;
   a leak orifice for providing communication between said enclosed volume and the ambient environment so that when said enclosed volume is immersed in an ambient environment containing a partial pressure of oxygen there is a tendency for the partial pressure of oxygen inside said enclosed volume to equalize with the partial pressure of oxygen of the ambient environment;
   an external circuit means coupled to said sensor cell for measuring an EMF across said sensor cell and coupled to said pump cell for applying an oscillatory pump cell current and thus producing a concurrent oscillation in the sensor cell EMF such that the period of the oscillations increases monotonically with the partial pressure of oxygen in the ambient and can be calibrated so as to be used as a sensor of the partial pressure of oxygen;
   said external circuit means having as an input the EMF generated by said sensor cell and having an output which causes oxygen to be withdrawn (injected) from (into) said enclosed volume, depending upon the polarity of the output current, until said sensor cell EMF reaches a predetermined reference value at which point the output current is changed so that the change of flux of oxygen is in the original direction, such changes in direction continuing in an oscillatory fashion; and
   said pump and sensor cells being formed of platelets of solid ionic conductors capable of conducting oxygen ions and including two electrode layers attached to opposing faces of each of said platelets, and lead wire attached to each of said electrodes for coupling said external circuit means to said pump and sensor cells.

2. An electrochemical apparatus as recited in claim 1 wherein said external circuit means includes measuring means for measuring the oscillatory period of the sensor cell EMF, and for converting the measured value of the oscillatory period to an electrical output proportional to the oscillatory period; and said external circuit means including processing means for processing the electrical output and including temperature compensation to produce a voltage proportional to the oxygen partial pressure of the ambient environment.

3. An electrochemical apparatus as recited in claim 1 wherein:

said associated supporting structure includes a hollow tube of material which is impervious to gases and retains a structural rigidity at elevated temperatures found in the exhaust gases of an internal combustion engine;

said pump cell and said sensor cell being affixed to opposing ends of said tube by a mounting means; and said pump and sensor cells being affixed to said tube so that one of said electrodes of each of said cells forms a part of the surface adjacent to said enclosed volume.

4. An electrochemical apparatus as recited in claim 1 further comprising a heater to maintain the temperature of said electrochemical structure and its adjacent gaseous surroundings so that a single calibration constant appropriate for the maintained range of temperatures can be used.

5. An electrochemical apparatus as recited in claim 1 wherein said external circuitry includes measurement means for measuring the temperature in the region of the sensor and adjusting the output of said external circuitry for variations in temperature.

6. A method for making a measurement of oxygen partial pressure in an ambient environment having other gaseous material including the steps of:

establishing an enclosed volume with restricted access to the ambient environment, the enclosed volume being bounded by a solid electrolyte electrochemical pump cell and a solid electrolyte electrochemical sensor cell, and the restricted access being sufficient so that when the enclosed volume is immersed in an ambient environment containing a partial pressure of oxygen there is a tendency for the partial pressure of oxygen inside the enclosed volume to equalize with the partial pressure of oxygen of the ambient environment;

applying to the pump cell an oscillatory pump cell current;

measuring an electrical output generated by the sensor cell in response to the oscillatory pump cell current at the pump cell;

determining the period of the oscillatory pump cell current to be determined by the time it takes for the sensor cell EMF to reach a first predetermined reference value traveling in a first increasing direction, and a second predetermined reference value traveling in a second decreasing direction; and calculating the oxygen partial pressure using a proportionality with the period of oscillation.

7. A method as recited in claim 6 further comprising the step of:

maintaining the temperature of the enclosed volume and adjacent regions so that a single calibration constant appropriate for the maintained range of temperatures can be used.

8. A method as recited in claim 7 further comprising the step of:

measuring the temperature in the region of the sensor cell and correcting the measurement of the oxygen partial pressure for the dependence of the temperature measuring output.

* * * * *